US011510863B2

(12) United States Patent
Daidoguchi et al.

(10) Patent No.: US 11,510,863 B2
(45) Date of Patent: Nov. 29, 2022

(54) WATER-IN-OIL EMULSION COSMETICS

(71) Applicant: SHISEIDO COMPANY, LTD., Tokyo (JP)

(72) Inventors: Noriko Daidoguchi, Kanagawa (JP); Kazuaki Suzuki, Kanagawa (JP)

(73) Assignee: SHISEIDO COMPANY, LTD., Tokyo (JP)

(*) Notice: Subject to any disclaimer, the term of this patent is extended or adjusted under 35 U.S.C. 154(b) by 223 days.

(21) Appl. No.: 16/470,868

(22) PCT Filed: Dec. 20, 2017

(86) PCT No.: PCT/JP2017/045780
§ 371 (c)(1),
(2) Date: Jun. 18, 2019

(87) PCT Pub. No.: WO2018/117172
PCT Pub. Date: Jun. 28, 2018

(65) Prior Publication Data
US 2019/0321281 A1 Oct. 24, 2019

(30) Foreign Application Priority Data
Dec. 21, 2016 (JP) .............................. JP2016-248307

(51) Int. Cl.
A61K 8/891 (2006.01)
A61K 8/06 (2006.01)
A61K 8/34 (2006.01)
A61K 8/44 (2006.01)
A61K 8/58 (2006.01)
A61K 8/60 (2006.01)
A61K 8/894 (2006.01)
A61K 8/895 (2006.01)
A61Q 19/00 (2006.01)

(52) U.S. Cl.
CPC .............. A61K 8/891 (2013.01); A61K 8/064 (2013.01); A61K 8/345 (2013.01); A61K 8/44 (2013.01); A61K 8/442 (2013.01); A61K 8/585 (2013.01); A61K 8/60 (2013.01); A61K 8/894 (2013.01); A61K 8/895 (2013.01); A61Q 19/00 (2013.01)

(58) Field of Classification Search
CPC ................................ A61K 8/064; A61K 8/895
See application file for complete search history.

(56) References Cited

U.S. PATENT DOCUMENTS

| 5,216,033 | A | 6/1993 | Pereira |
| 5,456,906 | A | 10/1995 | Powell et al. |
| 2004/0091437 | A1 | 5/2004 | Fack et al. |
| 2007/0128137 | A1 | 6/2007 | Yoshimi |
| 2007/0274932 | A1 | 11/2007 | Suginaka |
| 2008/0299058 | A1* | 12/2008 | Saito ............... A61K 8/31 424/59 |
| 2014/0356403 | A1 | 12/2014 | Zhu |
| 2014/0364394 | A1 | 12/2014 | Tamura et al. |

FOREIGN PATENT DOCUMENTS

| EP | 0407089 | A2 | 1/1991 |
| EP | 2939653 | A1 * | 11/2015 ............. A61K 8/345 |
| JP | S6422344 | A | 1/1989 |
| JP | H0344309 | A | 2/1991 |
| JP | H03217229 | A | 9/1991 |
| JP | 10-29912 | A | 2/1998 |
| JP | 2002087933 | A | 3/2002 |
| JP | 2005053834 | A | 3/2005 |
| JP | 2005220076 | A | 8/2005 |
| JP | 2005306823 | A | 11/2005 |
| JP | 2006232683 | A | * 9/2006 |
| JP | 2006232683 | A | 9/2006 |
| JP | 2006298796 | A | 11/2006 |
| JP | 2009517478 | A | 4/2009 |
| JP | 2010529104 | A | 8/2010 |
| JP | 2012188392 | A | 10/2012 |
| JP | 2013155163 | A | 8/2013 |
| JP | 2015505317 | A | 2/2015 |
| JP | 2015063483 | A | 4/2015 |
| JP | 2015168635 | A | 9/2015 |
| JP | 2016017074 | A | 2/2016 |
| JP | 2016130228 | A | 7/2016 |

OTHER PUBLICATIONS

KF-6017P: Emulsifying linear silicone, ShinEtsu Tech Data Sheet, 2014.*
KF-96A-6cs: Dimethyl silicone fluid, ShinEtsu Tech Data Sheet, 2013.*
KF-6017: Emulsifying linear silicone, ShinEtsu Technical Data Sheet, 2012.*
ShinEtsu, "Shin-Etsu Unique Materials", 2010. (Year: 2010).*
Extended European Search Report (EESR) dated Jul. 21, 2020 issued in the corresponding European Patent Application No. 17882894.3.
International Search Report dated Mar. 6, 2018 filed in PCT/JP2017/045780.
Written Opinion of the International Searching Authority (Form PCT/ISA/237) dated Mar. 6, 2018 filed in PCT/JP2017/045780; Partial English translation.

(Continued)

Primary Examiner — Gina C Justice
(74) Attorney, Agent, or Firm — Rankin, Hill & Clark LLP

(57) ABSTRACT

A water-in-oil emulsion cosmetic free of stickiness and oiliness, having semi-transparent or transparent appearance to effect feel of freshness, and able to provide moisturized feel is provided. The water-in-oil emulsion cosmetic contains (a) a solid moisturizer, (b) a polyether-modified silicone, and (c) a silicone oil having a refractive index in the range from 1.380 to 1.420 at 25° C., wherein a moisturizer content is 22 mass % or more relative to the total amount of the cosmetic.

9 Claims, No Drawings

(56) References Cited

OTHER PUBLICATIONS

Japanese Office Action dated Dec. 22, 2021 for corresponding Japanese Patent Application No. 2018-558047 and its English translation.
Chinese Office Action dated Jan. 6, 2022 for corresponding Chinese Patent Application No. 201780078530.X and its English translation.
Chinese Office Action dated Jun. 28, 2022 for Chinese Patent Application No. 201780078530.X; English translation.

* cited by examiner

WATER-IN-OIL EMULSION COSMETICS

TECHNICAL FIELD

The present disclosure relates to water-in-oil emulsion cosmetics.

BACKGROUND ART

There are various types of emulsion bases including oil-in-water type emulsions, water-in-oil type emulsions, or composite type emulsions. Among them, emulsion bases for water-in-oil emulsion cosmetics are known to provide more superior effects, such as skin protection effect, softening effect, and moisturizing effect, than oil-in-water emulsion cosmetics.

Water-in-oil emulsion cosmetics, in particular, water-in-oil creams, however, have problems, such as dragging during spreading, stickiness, and oiliness, depending on the formulation. For this reason, transparent appearance is desired to provide freshness in appearance. For example, Patent Literature 1 teaches a technique to provide a transparent water-in-oil cosmetic by matching refractive indices of the inner phase and the outer phase.

Further, Patent Literature 2 teaches a water-in-oil cosmetic using a silicone oil containing a volatile methyl siloxane fluid and a certain type of polydiorganosiloxane polyoxyalkylene copolymer, and containing a polyol to provide a transparent emulsion.

Still further, Patent Literature 3 teaches that a water-in-oil emulsion cosmetic that combines an organopolysiloxane, whose side chains have a polypeptide structure, with a cyclic silicone and a polyol is highly transparent.

CITATION LIST

Patent Literature

[PTL 1] Japanese Unexamined Patent Publication No. S64-22344
[PTL 2] Japanese Unexamined Patent Publication No. H3-44309
[PTL 3] Japanese Unexamined Patent Publication No. 2016-17074

SUMMARY OF DISCLOSURE

Technical Problem

As mentioned above, Patent Literature 1 achieves the transparency by matching the refractive indices of the inner phase and outer phase, and uses glycerin to match the refractive indices of the inner phase and outer phase. While this approach is successful in providing fresh appearance due to the transparency, the inclusion of glycerin hinders elimination of stickiness of the cosmetic itself. Patent Literature 2 and 3 are also deemed to achieve the transparency by matching the refractive indices of the inner phase and outer phase in technical point of view, and they use a liquid polyol to increase the refractive index of the aqueous phase. Thus, similarly to Patent Literature 1, the cosmetics of Patent Literature 2 and 3 still have the problem of stickiness of the cosmetics.

In view of the above-described circumstances, the present disclosure is directed to providing a water-in-oil emulsion cosmetic free of stickiness and oiliness, having semi-transparent or transparent appearance to effect feel of freshness, and able to provide moisturized feel.

Solution to Problem

A water-in-oil emulsion cosmetic of the present disclosure comprises:

(a) a solid moisturizer;
(b) a polyether-modified silicone; and
(c) a silicone oil having a refractive index in the range from 1.380 to 1.420 at 25° C., wherein a moisturizer content is 22 mass % or more relative to the total amount of the cosmetic.

The term "solid" as used herein with respect to the "(a) solid moisturizer" means that the moisturizer is in the form of powder, lump, or paste at room temperature (25° C.) and ordinary pressure (1 atm or $9.8 \times 10^4$ Pa), and the term "solid" is used in this sense in the disclosure. The solid moisturizer has hydrophilicity that allows the moisturizer to be stably dispersed in an aqueous phase.

It is preferred that the (a) solid moisturizer be a solid polyol and/or a solid amino acid. It is more preferred that the solid polyol and/or solid amino acid be at least one selected from bis-PEG-18 methyl ether dimethyl silane, polyethylene glycol having an average molecular weight in the range from 1,000 to 25,000, erythritol, trehalose, xylitol, trimethylglycine, and glycylglycine.

It is preferred that the (b) polyether-modified silicone have an HLB value in the range from 1 to 10. The term "HLB" as used herein refers to a value indicating a balance between hydrophilicity and lipophilicity (Hydrophilic-Lypophilic Balance).

It is more preferred that the (b) polyether-modified silicone have an HLB value in the range from 2 to 7.

It is preferred that the (b) polyether-modified silicone be at least one selected from polyoxyethylene methylpolysiloxane copolymer, cetyl dimethicone copolyol, poly(oxyethylene-oxypropylene) methylpolysiloxane copolymer, lauryl PEG-9 polydimethylsiloxyethyl dimethicone, and methylpolysiloxane cetyl methyl polysiloxane polyoxyethylene-oxypropylene) methylpolysiloxane copolymer.

It is preferred that the water-in-oil emulsion cosmetic of the disclosure further comprise a (d) silicone elastomer.

It is preferred that the (d) silicone elastomer be dimethicone crosspolymer or dimethicone/vinyl dimethicone crosspolymer.

The water-in-oil emulsion cosmetic of the disclosure may further comprise a (e) liquid moisturizer.

It is preferred that the water-in-oil emulsion cosmetic of the disclosure be semi-transparent or transparent.

Advantageous Effects of Disclosure

The water-in-oil emulsion cosmetic of the disclosure comprising: (a) solid moisturizer, (b) a polyether-modified silicone; and (c) a silicone oil having a refractive index in the range from 1.380 to 1.420 at 25° C., wherein a moisturizer content is 22 mass % or more relative to the total amount of the cosmetic, is free of stickiness, has semi-transparent or transparent appearance to effect feel of freshness, and is able to provide moisturized feel.

DESCRIPTION OF EMBODIMENTS

A water-in-oil emulsion cosmetic of the present disclosure comprises:
(a) a solid moisturizer;
(b) a polyether-modified silicone; and
(c) a silicone oil having a refractive index in the range from 1.380 to 1.420 at 25° C.,
wherein a moisturizer content is 22 mass % or more relative to the total amount of the cosmetic.

Now, individual components are described in detail.

(a) Solid Moisturizer

The (a) solid moisturizer is in the form of powder, lump, or paste at room temperature (25° C.) and ordinary pressure (1 atm or $9.8 \times 10^4$ Pa), and able to be stably dispersed or dissolved in an aqueous phase.

It is preferred that the (a) solid moisturizer be a solid polyol and/or solid amino acid. More specifically, it is more preferred that the (a) solid moisturizer be at least one selected from: sugars, such as sucrose, erythritol, trehalose, maltitol, and xylitol; polyethylene glycol having an average molecular weight in the range from 1,000 to 25,000; amino acids or amino acid derivatives, such as glycine, alanine, serine, arginine, aspartic acid, glutamic acid, arginine hydrochloride, trimethylglycine, and glycylglycine; and bis-PEG-18 methyl ether dimethyl silane (PEG: polyethylene glycol). These solid moisturizers may be used alone or in combination of two or more, as appropriate.

Examples of specific product names of commercially available products of bis-PEG-18 methyl ether dimethyl silane may include COSMETIC WAX 2501 (available from Dow Corning Toray Co., Ltd.) and SM4110P (available from KCC Corporation).

The inclusion of the solid moisturizer allows increasing the refractive index of the aqueous phase. Further, the solid moisturizer, which is dissolved in the water-in-oil emulsion cosmetic of the disclosure, is less likely to be sticky when it is dissolved and in the liquid phase, and also serves to mitigate stickiness which is otherwise caused by glycerin, or the like, when the glycerin, or the like, is contained alone in the water-in-oil emulsion cosmetic. The mechanism of the above-described effect of the solid moisturizer is not necessarily clear; however, the present inventor believes that, when a liquid moisturizer is remaining on the skin, feel of the liquid remaining on the skin causes feel of oiliness and stickiness; whereas the solid moisturizer remaining on the skin is in a more solid state and thus causes less sticky feel than a liquid moisturizer.

The content of the solid moisturizer is in the range from 0.1 to 30 mass %, and preferably from 0.5 to 25 mass %, relative to the total amount of the water-in-oil emulsion skin cosmetic. The content of the solid moisturizer in the range from 0.1 to 30 mass % allows providing semi-transparent or transparent appearance to effect feel of freshness, as well as even better feel during use.

(b) Polyether-Modified Silicone

The (b) polyether-modified silicone used in the disclosure is used to increase emulsion stability. The (b) polyether-modified silicone has a silicone chain (siloxane chain) as the main chain and a hydrophilic group having a polyether group as the side chains. Particularly, a polyether-modified silicone having a polyoxyalkylene group, such as polyoxyethylene (POE) or polyoxypropylene (POP) introduced into the silicone skeleton is preferred.

The polyether-modified silicone preferably has an HLB (Hydrophilic-Lypophilic Balance) value in the range from 1 to 10, and more preferably in the range from 2 to 7, where the HLB is calculated using Griffin's method. Specific examples of the polyether-modified silicone may include polyoxyethylene methylpolysiloxane copolymer (HLB=4.5), cetyl dimethicone copolyol (cetyl PEG/PPG10-1 dimethicone), poly(oxyethylene-oxypropylene) methylpolysiloxane copolymer (HLB=3.0), lauryl PEG-9 polydimethylsiloxyethyl dimethicone (HLB=3.0), and methylpolysiloxane cetyl methyl polysiloxane poly(oxyethylene-oxypropylene) methylpolysiloxane copolymer (HLB=5±1).

Examples of commercially available products of preferred polyether-modified silicones may include PEG-10 dimethicone (SILICONE KF-6017P, available from Shin-Etsu Chemical Co., Ltd.), BY11-030 and BY25-337 (available from Dow Corning Toray Co., Ltd.), and cetyl PEG/PPG10-1 dimethicone (ABIL® EM90, available from EVONIK).

It should be noted that, in the disclosure, a surfactant (emulsion) other than the polyether-modified silicone may also be used in combination within a range where the effect of the disclosure is not impaired.

The content of the polyether-modified silicone is in the range from 0.1 to 10 mass %, and preferably in the range from 0.2 to 5 mass %, relative to the total amount of the water-in-oil emulsion skin cosmetic. The content of the polyether-modified silicone in the range from 0.1 to 10 mass % allows providing a stable water-in-oil emulsion cosmetic, as well as even better feel during use.

(c) Silicone Oil

The silicone oil used in the disclosure has a refractive index in the range from 1.380 to 1.420 at 25° C. Using a silicone oil having a refractive index in this range allows decreasing the refractive index of the oil phase. The refractive index herein is a value measured with a digital refractive index meter (Type: RX5000α, available from ATAGO).

The silicone oil may be any of volatile silicone oils, non-volatile silicone oils, chained silicone oils, and cyclic silicone oils.

The volatile silicone oils refer to silicone oils that volatilize at room temperature (25° C.) and ordinary pressure (1 atm or $9.8 \times 10^4$ Pa). Specific examples of the volatile silicone oils may include: chained silicone oils (chained polysiloxanes), such as decamethyltetrasiloxane, hexamethyldisiloxane, and dodecamethylpentasiloxane; and cyclic silicone oils (cyclic polysiloxanes), such as cyclomethicone, hexamethylcyclotrisiloxane, octamethylcyclotetrasiloxane, decamethylcyclopentasiloxane, and methylpolycyclosiloxane. Examples of the non-volatile silicone oils may include dimethicones (dimethylpolysiloxanes) having a polymerization degree of 6 or more. The (c) silicone oil may be used alone or in combination of two or more, as appropriate.

Examples of commercially available products of the silicone oil may include KF-96A-6T (having a refractive index of 1.397), KF-96A-2CS (having a refractive index of 1.391), and SILICONE KF-96A-5000 (having a refractive index of 1.403) (all of which are available from Shin-Etsu Chemical Co., Ltd.).

The content of the silicone oil is preferably in the range from 5 to 30 mass %, and more preferably in the range from 10 to 20 mass %, relative to the total amount of the cosmetic. The content of the silicone oil in the range from 5 to 30 mass % allows providing a stable water-in-oil emulsion cosmetic, as well as even better feel during use.

Further, the content of the silicone oil is preferably 75 mass % or more relative to the total amount of the oil phase. The content of the silicone oil being 75 mass % or more facilitates maintaining the transparency of the cosmetic to enhance feel of freshness of the cosmetic.

(d) Silicone Elastomer

It is preferred that the water-in-oil emulsion cosmetic of the disclosure further contain a (d) silicone elastomer. The inclusion of the silicone elastomer allows providing even better fitting feel of the cosmetic on the skin, and increasing penetration. Preferred examples of the silicone elastomer may include, but are not limited to, one or two or more selected from the group consisting of dimethicone crosspolymer, dimethicone/vinyl dimethicone crosspolymer, dimethicone/phenyl vinyl dimethicone crosspolymer, vinyl dimethicone/lauryl dimethicone crosspolymer, lauryl polydimethylsiloxyethyl dimethicone/bis-vinyl dimethicone crosspolymer, alkyl (C30-45) cetearyldimethicone crosspolymer, and cetearyldimethicone crosspolymer. In view of providing an adequate feel on the skin, dimethicone crosspolymer or dimethicone/vinyl dimethicone crosspolymer are preferred.

The silicone elastomer is preferably contained in the form of a swelled product swelled with an oil that is liquid at ordinary temperature (25° C.). This further improves dispersibility and stability of the silicone elastomer. Examples of the liquid oil used to swell the silicone elastomer may include liquid silicone oils, liquid hydrocarbon oils, liquid ester oils, and liquid higher fatty acids. In particular, a liquid oil having low viscosity (for example, 100 m Pa·s or less) at ordinary temperature is preferred. Preferred viscosity range is from 1 to 100 mPa·s. The mixing ratio of the silicone elastomer to the liquid oil is preferably in the range from 5:95 to 40:60 in mass ratio.

As the liquid oil-swelled product of the silicone elastomer, those commercially available may be used, and examples of the commercially available products may include the following.

Examples of swelled products of dimethicone crosspolymer are 9040 SILICONE ELASTOMER BLEND, 9041 SILICONE ELASTOMER BLEND, 9045 SILICONE ELASTOMER BLEND, and EL-8040ID SILICONE ORGANIC BLEND (all of which are available from Dow Corning Toray Co., Ltd.).

The content of the silicone elastomer is preferably in the range from 0.1 to 5 mass % relative to the total amount of the cosmetic. This range allows providing even better feel during use.

A moisturizer content in the water-in-oil emulsion cosmetic of the disclosure is 22 mass % or more relative to the total amount of the cosmetic. It is more preferred that the content of the moisturizer be in the range from 22 to 45 mass % relative to the total amount of the cosmetic. The moisturizer may include only the (a) solid moisturizer, or may also include a (e) liquid moisturizer, which will be described below, in combination. In the case where the (e) liquid moisturizer is contained, the content of the (a) solid moisturizer is preferably 25 mass % or more relative to the total amount of the moisturizer. The content of the (a) solid moisturizer being 25 mass % or more allows further suppressing stickiness due to the liquid moisturizer. It is more preferred that the content of the (a) solid moisturizer be 30 mass % or more.

(e) Liquid Moisturizer

Examples of the liquid moisturizer may include dipropylene glycol, glycerin, 1,3-butylene glycol, and dipropylene glycol. The inclusion of the liquid moisturizer allows further improving the moisture-retaining property. In the technique taught in Patent Literature 1, the refractive index of the aqueous phase is adjusted by adding glycerin thereto. In this case, stickiness of the cosmetic cannot be suppressed. In contrast, the water-in-oil emulsion cosmetic of the disclosure has suppressed stickiness even when the water-in-oil emulsion cosmetic of the disclosure contains a liquid moisturizer. The reason is believed that the solid moisturizer contained in the water-in-oil emulsion cosmetic of the disclosure serves to suppress the stickiness due to the liquid moisturizer. The content of the liquid moisturizer is preferably in the range from 0.1 to 30 mass %, and more preferably in the range from 0.5 to 20 mass %, relative to the total amount of the cosmetic. The content of the liquid moisturizer in the range from 0.1 to 30 mass % allows increasing the moisturizing effect while suppressing the stickiness.

The oil phase component of the water-in-oil emulsion cosmetic of the disclosure may contain, besides the essential components (b) and (c), an oil that is commonly used in water-in-oil emulsion cosmetics within a range where uniformity of the oil phase is not impaired. Specifically, such an oil may be any of natural animal or vegetable oils and synthetic oils, and more specific examples thereof may include liquid oils, such as liquid paraffin or squalane, paste or solid hydrocarbons, waxes, higher fatty acids, higher alcohols, esters, glycerides, and silicone-based oils.

The content of the oil phase component in the water-in-oil emulsion cosmetic of the disclosure is in the range from 10 to 50 mass %. The content of the oil phase component being 10 mass % or more facilitates producing a water-in-oil emulsion cosmetic, and the content of the oil phase component being 50 mass % or less ensures a sufficient water content in the inner phase to provide more moisturized feel during use.

The aqueous phase of the water-in-oil emulsion cosmetic of the disclosure is mainly composed of water, and also contains various water-soluble components, besides the essential component (a). The content of the aqueous phase in the water-in-oil emulsion cosmetic of the disclosure is preferably within the range from 50 to 90 mass %, and more preferably 60 mass % or more in view of imparting moisturized feel. The content of the aqueous phase being 50 mass % or more allows enhancing the feature that the cosmetic contains water, and providing moisturized feel during use. The content of the aqueous phase being 90 mass % or less facilitates producing a water-in-oil emulsion cosmetic.

The water-in-oil emulsion cosmetic of the disclosure may contain a powder. Preferred examples of the powder, in view of transparency, may include methyl siloxane network polymer and cross-linked silicone network silicone block copolymer.

Besides the above-described essential components, the water-in-oil emulsion cosmetic of the disclosure may contain commonly used aqueous components and oil-based components, such as antiseptic, antioxidant, ultraviolet absorber, effective ingredients, perfume, fragrance retaining agent, thickener, coloring pigments, photoluminescent pigments, organic powders, hydrophobizing pigments, and tar pigments, within a range where the effect of the disclosure is not impaired.

Specific examples of the water-in-oil emulsion cosmetic of the disclosure include emulsion-type or cream-type products, such as milky lotion, skin care cream, hair cream, liquid foundation, eyeliner, mascara, and eye shadow, which are made from the above-described components according to usual processes.

EXAMPLES

Next, the present disclosure is more specifically described with reference to examples. The following examples are not intended to limit the disclosure.

Examples 1 to 5 and Comparative Examples 1 to 4

Samples of skin care cream, as a water-in-oil emulsion cosmetic, were produced according to the formulations shown in Table 1, and the resulting samples of skin care cream were evaluated according to criteria shown below from the view points of transparency and feel during use (stickiness, oiliness, and moisturized feel). The results are shown in Table 1 along with the formulations, where the content of each component is in mass %.

Details, such as product names, of the raw materials shown in Table 1 are as follows.

\* Polyoxyethylene methylpolysiloxane copolymer: SILICONE KF-6017P (available from Shin-Etsu Chemical Co., Ltd.)

\*\* Methyl siloxane network polymer: TOSPEARL 3000A (available from Momentive Performance Materials Japan LLC)

\*\*\* Cross-linked silicone network silicone block copolymer: KSP-102 (available from Shin-Etsu Chemical Co., Ltd.)

Transparency

Transparency of the composition of each example was visually observed and evaluated according to the criteria shown below.

AA: The composition was transparent and letters were able to be seen clearly therethrough.

A: The composition exhibited a trace of cloudiness but was almost transparent, and letters were able to be seen clearly therethrough.

B: The composition was slightly cloudy and letters were not able to be seen clearly therethrough but identifiable.

C: The composition was cloudy and transparent, and letters were not identifiable therethrough.

Feel During Use

The composition of each example was evaluated for feel during use (stickiness, oiliness, and moisturized feel) according to the criteria shown below based on answers to questionnaire.

Evaluation Criteria

AA: 18 or more people among 20 people answered "good."
A: 12 to 17 people among 20 people answered "good."
B: 5 to 11 people among 20 people answered "good."
C: Less than 4 people among 20 people answered "good."

TABLE 1

| | | | Ex. 1 | Ex. 2 | Ex. 3 | Ex. 4 | Ex. 5 | Comp. Ex. 1 | Comp. Ex. 2 | Comp. Ex. 3 | Comp. Ex. 4 |
|---|---|---|---|---|---|---|---|---|---|---|---|
| Aqueous phase | Water | Ion-exchanged water | balance | balance | balance | balance | balance | balance | balance | balance | balance |
| | Moisturizer | Dynamite glycerin | | 10 | 10 | 10 | 10 | 30 | 5 | | |
| | | Dipropylene glycol | | 10 | 10 | 10 | 10 | 8 | | | |
| | | Xylitol | 10 | | | | | | | 10 | 10 |
| | | Erythritol | 5 | 5 | 5 | 5 | 5 | | 5 | 5 | 5 |
| | | Trimethylglycine | 5 | 5 | 5 | 5 | 5 | | 5 | 5 | 5 |
| | | Glycylglycine | | | | | | | | | |
| | | PEG-20 (average molecular weight: 1000) | 5 | | | | | | | 5 | 5 |
| | | PEG-150 (average molecular weight: 6000) | | 3 | 3 | 3 | | | | | |
| | | PEG-400 (average molecular weight 20000) | | | | | 1 | | | | |
| | | Bis-PEG-18 methyl ether dimethylsilane | 5 | 3 | 3 | 3 | 3 | | | 5 | 5 |
| | Medicament | Tranexamic acid | | | | 1 | | | | | |
| | | Potassium 4-methoxysalicylate | | | | | 1 | | | | |
| | | 1-piperidine propionic acid | | | | | | 1 | | | |
| | Chelating-agent | EDTA-3Na2H$_2$O | 0.02 | 0.02 | 0.02 | 0.02 | 0.02 | 0.02 | 0.02 | 0.02 | 0.02 |
| | Stabilizer | Sodium chloride | 1 | 1 | 1 | 1 | 1 | 1 | 1 | 1 | 1 |
| | Antiseptic | Phenoxyethanol | 0.5 | 0.5 | 0.5 | 0.5 | 0.5 | 0.5 | 0.5 | 0.5 | 0.5 |
| Oil phase | Polyether-modified silicone | Polyoxyethylene methylpolysiloxane copolymer (HLB 4.5)* | 1 | 1 | | 1 | 1 | 1 | 1 | 1 | |
| | | Lauryl PEG-9 polydimethylsiloxyethyl dimethicone (HLB 3) | | | 1 | | | | | | |
| | | PEG/PPG-19/19 dimethicone (HLB 3) | 0.75 | 0.75 | 0.75 | | 0.75 | 0.75 | 0.75 | 0.75 | |
| | | Methylpolysiloxane cetyl methyl polysiloxane poly(oxyethylene-oxypropylene) methylpolysiloxane copolymer (HLB 5) | | | | 1.5 | | | | | |
| | Surfactant | Diglyceryl diisostearate | | | | | | | | | 2.5 |
| | Silicone oil | Dimethicone (refractive index: 1.397) | 10 | | | | | 10 | 10 | | |
| | | Cyclomethicone (refractive index: 1.396) | | 13.8 | 14.3 | 14.3 | 14.3 | | | 10 | 10 |
| | | Methylphenyl polysiloxane (refractive index: 1.5) | | | | | | | | | |
| | | Decamethylcyclopentasiloxane (refractive index: 1.396) | | | | 0.75 | | | | | |
| | Hydrocarbon oil | Hydrogenated isobutene | 0.75 | 0.75 | | | 0.75 | 0.75 | 0.75 | 0.75 | |
| | Silicone elastomer | Dimethicone crosspolymer | | | 0.7 | 0.7 | 0.7 | | | | |
| | | Dimethicone/vinyl dimethicone crosspolymer | | 1.2 | | | | | | | |

TABLE 1-continued

|  |  | Ex. 1 | Ex. 2 | Ex. 3 | Ex. 4 | Ex. 5 | Comp. Ex. 1 | Comp. Ex. 2 | Comp. Ex. 3 | Comp. Ex. 4 |
|---|---|---|---|---|---|---|---|---|---|---|
| Powder | Methyl siloxane network polymer** |  | 1 |  |  |  |  |  |  |  |
|  | Cross-linked silicone network silicone block copolymer*** |  |  |  | 1 |  |  |  |  |  |
|  | Total | 100 | 100 | 100 | 100 | 100 | 100 | 100 | 100 | 100 |
| Evaluation | Transparency | AA | A | AA | AA | AA | A | C | C | not able to be prepared |
|  | Feel during use | A | A | A | A | A | C | B | C | — |

As shown in Table 1, the water-in-oil emulsion cosmetic of the disclosure was free of stickiness and oiliness, exhibited transparent appearance to effect feel of freshness, and provided moisturized feel. Although Example 1 did not contain glycerin or liquid polyol, it exhibited good transparency and provided satisfactory feel during use. Further, as exhibited by Examples 2 to 5, the water-in-oil emulsion cosmetic of the disclosure containing glycerin or liquid polyol was also free of stickiness and oiliness and provided good feel during use.

On the other hand, Comparative Example 1, which contained only a liquid moisturizer, exhibited stickiness and poor penetration into the skin. The composition of Comparative Example 2, in which the content of the moisturizer relative to the total amount of the cosmetic was low, was cloudy and exhibited stickiness. The composition of Comparative Example 3, which used a silicone oil having a refractive index out of the range defined in the disclosure, was also cloudy and exhibited stickiness and oiliness. The composition of Comparative Example 4, in which the surfactant was not a polyether-modified silicone, was not able to be prepared.

The invention claimed is:

1. A water-in-oil emulsion cosmetic comprising:
(a) a solid moisturizer;
(b) a polyether-modified silicone in an amount within a range from 0.1 to 10 wt % relative to the total amount of the cosmetic;
(c) a silicone oil having a refractive index in the range from 1.380 to 1.420 at 25° C.;
(d) a silicone elastomer; and
(e) a liquid moisturizer,
wherein a moisturizer content is 22 mass % or more relative to the total amount of the cosmetic,
the (a) solid moisturizer is a solid polyol and/or a solid amino acid, the solid moisturizer includes at least bis-PEG-18 methyl ether dimethyl silane and is contained in an amount within a range from 0.1 to 25 wt % relative to the total amount of the cosmetic,
the (d) silicone elastomer is contained in an amount within a range from 0.1 to 5 wt % relative to the total amount of the cosmetic in a form of a swelled product swelled with a liquid oil that is liquid at room temperature,
a mixing ratio of the (d) silicone elastomer to the liquid oil is in the range from 5:95 to 40:60 in mass ratio,
the liquid oil used to swell the (d) silicone elastomer includes at least one selected from a group consisting of a liquid silicone oil, a liquid hydrocarbon oil, a liquid ester oil and a liquid higher fatty acids, and
a content of the (e) liquid moisturizer is 0.1 to 20 mass % relative to the total amount of the cosmetic.

2. The water-in-oil emulsion cosmetic as claimed in claim 1, wherein the solid polyol and/or solid amino acid further includes at least one selected from a group consisting of polyethylene glycol having an average molecular weight in the range from 1,000 to 25,000, erythritol, trehalose, xylitol, trimethylglycine, and glycylglycine.

3. The water-in-oil emulsion cosmetic as claimed in claim 1, wherein the (b) polyether-modified silicone has an HLB value in the range from 1 to 10.

4. The water-in-oil emulsion cosmetic as claimed in claim 3, wherein the (b) polyether-modified silicone has an HLB value in the range from 2 to 7.

5. The water-in-oil emulsion cosmetic as claimed in claim 4, wherein the (b) polyether-modified silicone is at least one selected from polyoxyethylene methylpolysiloxane copolymer, cetyl dimethicone copolyol, poly(oxyethylene-oxypropylene) methylpolysiloxane copolymer, lauryl PEG-9 polydimethylsiloxyethyl dimethicone, and methylpolysiloxane cetyl methyl polysiloxane poly(oxyethylene-oxypropylene) methylpolysiloxane copolymer.

6. The water-in-oil emulsion cosmetic as claimed in claim 1, wherein the (d) silicone elastomer is dimethicone crosspolymer or dimethicone/vinyl dimethicone crosspolymer.

7. The water-in-oil emulsion cosmetic as claimed in claim 1 being semi-transparent or transparent.

8. The water-in-oil emulsion cosmetic as claimed in claim 2, wherein the (b) polyether-modified silicone has an HLB value in the range from 1 to 10.

9. The water-in-oil emulsion cosmetic as claimed in claim 5 being semi-transparent or transparent.

* * * * *